| United States Patent [19] | [11] 4,044,125 |
|---|---|
| Walkling | [45] Aug. 23, 1977 |

[54] METHOD OF STABILIZING ACETYLSALICYLIC ACID IN THE PRESENCE OF D-PROPOXYPHENE HYDROCHLORIDE AND COMPOSITIONS THEREOF

[75] Inventor: Walter D. Walkling, Huntingdon Valley, Pa.

[73] Assignee: Eli Lilly and Company, Indianapolis, Ind.

[21] Appl. No.: 669,059

[22] Filed: Mar. 22, 1976

Related U.S. Application Data

[60] Continuation-in-part of Ser. No. 597,130, July 18, 1975, abandoned, which is a division of Ser. No. 177,870, Sept. 3, 1971, abandoned, which is a continuation-in-part of Ser. No. 72,504, Sept. 15, 1970, abandoned.

[51] Int. Cl.² .................. A61K 31/61; A61K 31/615; A61K 31/625

[52] U.S. Cl. .................................. 424/232; 424/233; 424/234

[58] Field of Search ........................... 424/32, 34, 233

[56] References Cited

U.S. PATENT DOCUMENTS 2,101,867  12/1937  Miller et al. ......................... 424/233

OTHER PUBLICATIONS

Physician's Desk Reference, 1970, pp. 831–832.

*Primary Examiner*—Stanley J. Friedman
*Attorney, Agent, or Firm*—Ralph W. Ernsberger; Everet F. Smith

[57] ABSTRACT

Method of inhibiting the hydrolysis of acetylsalicyclic acid in the presence of d-propoxyphene hydrochloride in pharmaceutical compositions comprising admixing the hydrochloride of one of the 23 naturally occuring amino acids therewith, and compositions containing such amino acid hydrochloride, acetylsalicylic acid and d-propoxyphene hydrochloride.

5 Claims, No Drawings

METHOD OF STABILIZING ACETYLSALICYLIC ACID IN THE PRESENCE OF D-PROPOXYPHENE HYDROCHLORIDE AND COMPOSITIONS THEREOF

CROSS-REFERENCE

This application is a continuation in part of copending patent application, Ser. No. 597,130, filed July 18, 1975 which was a divisional of patent application, Ser. No. 177,870, filed Sept. 3, 1971, which was a continuation-in-part of application, Ser. No. 72,504, filed Sept. 15, 1970, all now abandoned.

BACKGROUND OF THE INVENTION

1. Field of Invention

This invention relates to the stabilization of acetylsalicyclic acid in the presence of d-propoxyphene hydrochloride in pharmaceutical compositions. Specifically, it relates to the inhibition of the hydrolysis of said acetylsalicyclic acid in such compositions.

2. Description of the Prior Art

Combinations of therapeutic agents to provide single unit dosage forms which are convenient for administering pharmaceutical compositions containing more than one active agent in a single dose are old in the pharmaceutical art, and many of these contain, among other ingredients, acetylsalicylic acid. Acetylsalicylic acid, hereinafter referred to as aspirin, is an analgesic of unquestioned merit employed around the world for the alleviation of pain associated with simple headaches, neuralgia, neuritis, rheumatism, and assorted other afflications of the body. Aspirin is a common ingredient in pharmaceutical dosage forms containing combinations of analgesic agents, and these combinations have been utilized for decades to improve the scope of analgesic therapy.

Aspirin is odorless and in the dry state is stable, but in the presence of moisture slowly hydrolyzes into acetic and salicylic acids and takes on the characteristic odor of acetic acid. In pharmaceutical compositions, even a small amount of aspirin hydrolysis is sufficient to product the disagreeably pungent odor of acetic acid and destroy the pharmaceutical elegance and patient acceptability of the composition. A free salicylic acid content of more than 3 percent exceeds the USP XVIII (1970) standard, and renders the composition containing aspirin unsaleable.

The analgesic d-propoxyphene hydrochloride, U.S. Pat. No. 2,728,779 (1955), has gained wide acceptance as a drug for the treatment of pain associated with traumas, particularly since it is not addictive. The combination of aspirin, d-propoxyphene hydrochloride, phenacetin and caffeine has been sold throughout most of the world for more than a decade, and has become established as a superior treatment for many uncomplicated manifestations of pain.

Pharmaceutical compositions comprising aspirin and d-propoxyphene hydrochloride, with and without other ingredients in combination therewith, especially those which have been filled into gelatin capsules to provide a unit dosage form, have been particularly susceptible to the hydrolysis of the aspirin and the concomitant development of the pungent odor of acetic acid, thus making the pharmaceutical form totally unacceptable to the patient. One such multiple component pharmaceutical composition is constituted as follows: aspirin, 40.0 percent; d-propoxyphene hydrochloride, 11.4 percent; phenacetin, 28.4 percent; caffeine, 5.7 percent; and starch, 14.5 percent. Another is constituted simply of aspirin, 52.4 percent; d-propoxyphene hydrochloride, 10.5 percent; and kaolin, 37.1 percent. Still another is composed of aspirin, 58.0 percent; d-propoxyphene hydrochloride, 5.7 percent, phenaglycodol, 26.8 percent; and silica gel, 9.5 percent.

In the pharmaceutical compositions illustrated above, the common denominator is the combination of aspirin and de-propoxyphene hydrochloride. The commingling of d-propoxyphene hydrochloride with aspirin in pharmaceutical compositions has uniformly resulted in an increase in both the rate and amount of aspirin hydrolysis. The exact reason for this phenomenon is not completely understood. Several attempts have been made to overcome the hydrolysis problem, notably by forming a small tablet or nonpareil type pellet of d-propoxyphene hydrochloride to isolate the latter from the aspirin or by the coacervate coating of the aspirin with ethyl cellulose to segregate it from the d-propoxyphene hydrochloride. Neither approach entirely corrects the difficulty. An effective method for inhibiting the hydrolysis of aspirin in the presence of d-propoxyphene hydrochloride in pharmaceutical compositions would, therefore, constitute a much-needed advance in the art.

SUMMARY

This method provides a process for substantially inhibiting the hydrolysis of aspirin to salicylic acid and acetic acid in the presence of d-propoxyphene hydrochloride in pharmaceutical compositions, which process comprises admixing the hydrochloride of one of the 23 naturally occuring amino acids into such compositions. Compositions stabilized against the hydrolysis of acetylsalicylic acid are provided.

DESCRIPTION OF THE PREFERRED EMBODIMENT

This invention relates to a method for stabilizing pharmaceutical compositions comprising d-propoxyphene hydrochloride and acetylsalicylic acid.

Quite unexpectedly, it has now been discovered that the hydrolysis of acetylsalicylic acid, hereinafter referred to as aspirin, to yield free acetic and salicylic acids in pharmaceutical compositions in which d-propoxyphene hydrochloride is present can be substantially inhibited, or even essentially prevented, by admixing the hydrochloride of a compound selected from the group having as a general formula either

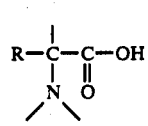 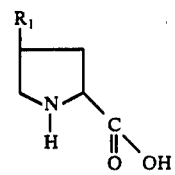

Wherein

R is hydrogen, methyl, isopropyl, butyl, isobutyl, secbutyl, hydroxymethyl, 1-hydroxyethyl, carboxymethyl, carboxyethyl, carboxy-(1-hydroxy)ethyl, aminobutyl, methylthioethyl, mercaptomethyl, carboxy-(2-aminoethyl)dithiomethyl, p-hydroxyphenyl, benzyl, indolylmethyl, guanidopropyl, imidazolylmethyl and ureidopropyl; and, $R_1$ is hydrogen or hydroxyl.

The useful compounds described above comprise the 23 naturally occurring amino acids popularly known as essential amino acids. The designation "essential" is not intended to denote indispensable as contrasted with dispensable as applied to human nutritional requirements, but incorporates those amino acids which are characterized as both, and includes the following naturally occurring amino acids listed by both the common and scientific name.

Glycine, 2-aminoacetic acid;
Alanine, 2-aminopropanoic acid;
Valine, 2-amino-3-methylbutanoic acid;
Norleucine, 2-aminohexanoic acid;
Leucine, 2-amino-4-methylpentanoic acid;
Isoleucine, 2-amino-3-methylpentanoic acid;
Serine, 2-amino-3-hydroxypropanoic acid;
Threonine, 2-3-hydroxybutanoic acid;
Aspartic acid, aminosuccinic acid;
Glutamic acid, 2-aminopentanedioic acid;
Hydroxyglutamic acid, 2-amino-3-hydroxypentanedioic acid;
Lysine, 2,6-diaminohexanoic acid;
Methionine, 2-amino-4-methylthiobutanoic acid;
Cysteine, 2-amino-3-mercaptopropionic acid;
Cystine, 3,3'-dithiobis(2-aminopropanoic acid);
Tyrosine, 2-amino-p-hydroxyhydrocinnamic acid;
Phenylalanine, 2-2-amino-3-phenylpropanoic acid;
Tryptophane, 2-amino-3-indolylpropanoic acid;
Arginine, 2-amino-5-guanidovaleric acid;
Histidine, 2-amino-3-(5-imidazolyl)propanoic acid;
Citrulline, 2-amino-5-ureidovaleric acid;
Proline, 2-pyrrolidinecarboxylic acid;
Hydroxyproline, 4-hydroxy-2-pyrrolidinecarboxylic acid.

The term naturally occuring amino acids will be employed hereinafter to denote the above described class of compounds.

The hydrochlorides of naturally occurring amino acids useful in this invention are prepared by reacting such amino acids with hydrochloric acid in either an aqueous or ethanolic solution and are purified by crystallization following procedures well known to those skilled in the art. The scope of this invention embraces both the dihydrochlorides and monohydrochlorides of the diaminocarboxylic acids, arginine, lysine and citrulline.

Naturally occurring amino acids useful as the hydrochloride in the novel processes and compositions of this invention, occur naturally in the L-form. The DL-amino acid racemic mixtures have been synthesized, and the D-form is recognized. All three forms are available in the form of their hydrochloride salts, and as the hydrochloride salts are operative in the present invention. The L-form is the most commercially available of the forms of naturally occurring amino acid hydrochlorides and represents the preferred embodiment herein exemplified.

In the practice of the instant invention, it has been found that the quantity of the amino acid hydrochloride required to inhibit the hydrolysis of the aspirin is related to the amount of d-propoxyphene hydrochloride present in the aspirin/d-propoxyphene hydrochloride combination. Effective hydrolysis inhibition is achieved when a naturally occurring amino acid as the hydrochloride is admixed into the pharmaceutical composition in an amount of from about 5 to about 130 percent by weight of the amount of d-propoxyphene hydrochloride present. Preferably, the naturally ocurring amino acid hydrochloride is employed in an amount of from about 5 to about 50 percent of the quantity of d-propoxyphene hydrochloride present. The naturally occurring amino acid hydrochloride employed in the useful processes of this invention can be admixed with the other ingredients in the pharmaceutical composition in any order and an effective inhibition of aspirin hydrolysis will be achieved. Preferably, the naturally occurring amino acid hydrochloride and d-propoxyphene hydrochloride are intimately admixed before commingling with the aspirin. In an especially preferred embodiment of the present invention, a naturally occurring amino acid hydrochloride and d-propoxyphene hydrochloride are intimately admixed and granulated together with a pharmaceutically acceptable solvent in which one of the ingredients is substantially soluble, such as water, methanol, ethanol, isopropanol, acetone, methylethyl ketone, methylisobutyl ketone, chloroform, methylene chloride, trichloroethylene, trichlorofluoromethane, 1,2-dichloro-1,1,2,2-tetrafluoroethane, and the like, preferably ethanol, the solvent removed therefrom by evaporation, and the dried granules commingled with the aspirin.

The admixing of a naturally occurring amino acid hydrochloride, preferably in the L-form, with the aspirin and d-propoxyphene hydrochloride combination results in a many-fold decrease in the rate and amount of aspirin hydrolysis in the presence of moisture.

An eminently satisfactory utilization of a naturally occurring amino acid hydrochloride for the inhibition of aspirin hydrolysis is accomplished by substituting L-glutamic acid hydrochloride for all of the inert ingredient, starch, in one of the pharmaceutical compositions illustrated above, resulting in a pharmaceutical composition composed of: aspirin, 40.0 percent; d-propoxyphene hydrochloride, 11.4 percent phenacetin, 28.4 percent; caffeine, 5.7 percent; and L-glutamic acid hydrochloride, 14.5 percent. The rate of hydrolysis of aspirin in such a composition decreased from 70 to 90 percent by comparison with the unstabilized composition.

When L-lysine dihydrochloride is added in an amount of about 18 percent of the d-propoxyphene hydrochloride content in a pharmaceutical composition containing aspirin, 52.4 percent; d-propoxyphene hydrochloride 10.5 percent; and kaolin, 37.1 percent, resulting in a pharmaceutical composition in which the naturally occurring amino acid as the hydrochloride comprised about 2 percent of the total, the rate of hydrolysis is decreased more than 50 percent.

Other compatible active agents and pharmaceutically acceptable inert ingredients can coexist in the pharmaceutical composition comprising the combination of aspirin, d-propoxyphene hydrochloride and naturally occurring amino acid hydrochloride, or the latter combination can comprise the sole contents of the composition. In either case, the rate of aspirin hydrolysis will be significantly retarded in the presence of the naturally occurring amino acid hydrochloride.

Other pharmaceutically acceptable water soluble salts of naturally occurring amino acids, such as phosphate, sulfate, and the like can also be effectively employed to impede the hydrolysis of aspirin in pharmaceutical compositions comprising d-propoxyphene hydrochloride and aspirin.

The novel pharmaceutical compositions of this invention can be filled into gelatin capsules or formed into compressed tablets, by processes known to those skilled in the art, in suitable quantities to provide unit dosage forms containing the appropriate amounts of the therapeutic agents for oral administration.

This invention is further illustrated by the following examples.

EXAMPLE 1

Pharmaceutical compositions comprising aspirin and d-propoxyphene hydrochloride were prepared according to the following formulae and filled into gelatin capsules. The filled capsules were stored a 50° C. for 4 days and the contents analyzed for free salicylic acid using the procedure outlined on page 607 of N.F. XIII (1970). The percent salicylic acid found is shown in Table I below:

FORMULA A

| Ingredient | Amount |
|---|---|
| Aspirin | 227 g. |
| Phenacetin | 162 g. |
| Caffeine | 32 g. |
| d-Propoxyphene hydrochloride | 65 g. |
| Starch | 84 g. |

The ingredients were admixed together in a laboratory size ribbon blender for 15 minutes and filled into size 0 gelatin capsules, each capsule containing 579 mg.

FORMULA B

| Ingredient | Amount |
|---|---|
| Aspirin | 227 g. |
| Phenacetin | 162 g. |
| Caffeine | 32 g. |
| d-Propoxyphene hydrochloride | 65 g. |
| Kaolin | 84 g. |

The ingredients were admixed together in a laboratory size ribbon blender for 15 minutes and filled into size 0 gelatin capsules, each capsule containing 570 mg.

FORMULA C

| Ingredient | Amount |
|---|---|
| Aspirin | 227 g. |
| Phenacetin | 162 g. |
| Caffeine | 32 g. |
| d-Propoxyphene hydrochloride | 65 g. |
| L-Glutamic acid hydrochloride | 84 g. |

The ingredients were admixed together in a laboratory size ribbon blender for 15 minutes and filled into size 0 gelatin capsules, each capsule containing 570 mg.

FORMULA D

| Ingredient | Amount |
|---|---|
| Aspirin | 227 g. |
| Phenacetin | 163 g. |
| Caffeine | 32 g. |
| d-Propoxyphene hydrochloride | 65 g. |
| L-Glutamic acid hydrochloride | 30 g. |
| Starch | 54 g. |

The d-propoxyphene hydrochloride and L-glutamic acid hydrochloride were admixed together in a Hobart mixer for 5 minutes, and 10 ml. of ethyl alcohol were added to the blended powder and the mixer was run for another 5 minutes. The moistened mass was removed from the mixer, passed through a No. 6 mesh (U.S.) screen, and spread on trays. The ethyl alcohol was removed from the granulation in vacuo for 2 hours at 25° C. The dried granules were worked through a 16 mesh (U.S.) screen and added to a laboratory size ribbon blender. The remainder of the ingredients were added to the blender and admixed together for 15 minutes and then filled into size 0 gelatin capsules, each capsule containing 570 mg.

FORMULA E

| Ingredient | Amount |
|---|---|
| Aspirin | 227 g. |
| Phenacetin | 162 g. |
| Caffeine | 32 g. |
| d-Propoxyphene hydrochloride | 65 g. |
| L-Glutamic acid hydrochloride | 30 g. |
| Kaolin | 54 g. |

The ingredients were processed and combined as described under Formula D above.

FORMULA F

| Ingredient | Amount |
|---|---|
| Aspirin | 227 g. |
| Phenacetin | 162 g. |
| Caffeine | 32 g. |
| d-Propoxyphene hydrochloride | 65 g. |
| L-Glutamic acid hydrochloride | 15 g. |
| Starch | 69 g. |

The ingredients were processed and combined as described under Formula D above.

FORMULA G

| Ingredient | Amount |
|---|---|
| Aspirin | 227 g. |
| Phenacetin | 162 g. |
| Caffeine | 32 g. |
| d-Propoxyphene hydrochloride | 65 g. |
| L-Glutamic acid hydrochloride | 15 g. |
| Kaolin | 69 g. |

The ingredients were processed and combined as described under Formula D above.

TABLE I

FREE SALICYLIC ACID CONTAINED IN PHARMACEUTICAL COMPOSITIONS AFTER FOUR DAYS STORAGE IN FILLED CAPSULES AT 50° C.

| Formula | d-Propoxyphene Hydrochloride mg./Capsule | L-Glutamic Acid Hydrochloride mg./Capsule | L-Glutamic Acid d-Propoxyphene Hydrochloride | % Free Salicylic Acid Contained in Pharmaceutical Compositions |
|---|---|---|---|---|
| A | 65 | None | — | 2.93 |
| B | 65 | None | — | 2.28 |
| C | 65 | 84 | 129 | 0.67 |
| D | 65 | 30 | 46 | 0.25 |
| E | 65 | 30 | 46 | 0.30 |
| F | 65 | 15 | 23 | 0.55 |

TABLE I-continued
FREE SALICYLIC ACID CONTAINED IN PHARMACEUTICAL COMPOSITIONS AFTER FOUR DAYS STORAGE IN FILLED CAPSULES AT 50° C.

| Formula | d-Propoxyphene Hydrochloride mg./Capsule | L-Glutamic Acid Hydrochloride mg./Capsule | L-Glutamic Acid d-Propoxyphene Hydrochloride | % Free Salicylic Acid Contained in Pharmaceutical Compositions |
|---|---|---|---|---|
| G | 65 | 15 | 23 | 0.66 |

The data clearly shows that the commingling of L-glutamic acid hydrochloride with aspirin and d-propoxyphene hydrochloride results in a 3- to 10-fold reduction in the rate of aspirin hydrolysis as measured by the development of free salicylic acid in the pharmaceutical composition.

EXAMPLE 2

Pharmaceutical compositions comprising aspirin and d-propoxyphene hydrochloride were prepared containing respectively 84 mg. per capsule of glutamic acid hydrochloride in the D-form, DL-form, and L-form. The capsules were stored at 50° C. for 4 days, and the contents were analyzed for free salicylic acid using the procedure outlined on page 607 of N.F. XIII (1970). Table II shows the percent salicylic acid found.

TABLE II
FREE SALICYLIC ACID CONTAINED IN PHARMACEUTICAL COMPOSITIONS AFTER FOUR DAYS STORAGE IN FILLED CAPSULES AT 50° C.

| Aspirin mg./Capsule | d-Propoxyphene Hydrochloride mg./Capsule | Glutamic Acid Hydrochloride mg./Capsule | Glutamic Acid Hydrochloride Form Used | % Free Salicylic Acid Contained in Pharmaceutical Compositions |
|---|---|---|---|---|
| 227 | 65 | None | — | 2.93 |
| 227 | 65 | None | — | 2.28 |
| 227 | 65 | 84 | L-form | 0.67 |
| 227 | 65 | 84 | DL-form | 1.47 |
| 227 | 65 | 84 | D-form | 1.25 |

The data in Table II show that all three forms of glutamic acid hydrochloride were effective in inhibiting the hydrolysis of aspirin in the presence of d-propoxyphene hydrochloride, the L-form showing the greatest effect, as measured by a lessening of the amount of free salicylic acid contained in the pharmaceutical composition in which glutamic acid hydrochloride was included as one of the ingredients.

EXAMPLE 3

Pharmaceutical compositions comprising aspirin, d-propoxyphene hydrochloride, and L-lysine dihydrochloride were prepared according to the following formulae and filled into gelatin capsules. The filled capsules were stored at 50° C. for 4 days and the contents analyzed for free salicylic acid using the procedure outlined on page 607 of N.F. XIII (1970). The percent salicylic acid found is shown in Table III below:

FORMULA H

| Ingredient | Amount |
|---|---|
| Aspirin | 325 g. |
| d-Propoxyphene hydrochloride | 65 g. |
| Starch | 230 g. |

The ingredients were admixed together in a laboratory size ribbon blender for 15 minutes and filled into size 0 gelatin capsules, each capsule containing 620 mg.

FORMULA J

| Ingredient | Amount |
|---|---|
| Aspirin | 325 g. |
| d-Propoxyphene hydrochloride | 65 g. |
| Starch | 228 g. |
| L-Lysine dihydrochloride | 2 g. |

The ingredients were admixed together in a laboratory size ribbon blender for 15 minutes and filled into size 0 gelatin capsules, each capsule containing 620 mg.

FORMULA K

| Ingredient | Amount |
|---|---|
| Aspirin | 325 g. |
| d-Propoxyphene hydrochloride | 65 g. |
| Starch | 226 g. |
| L-Lysine dihydrochloride | 4 g. |

The ingredients were admixed together in a laboratory size ribbon blender for 15 minutes and filled into size 0 gelatin capsules, each capsule containing 620 mg.

FORMULA L

| Ingredient | Amount |
|---|---|
| Aspirin | 325 g. |
| d-Propoxyphene hydrochloride | 65 g. |
| Starch | 224 g. |
| L-Lysine dihydrochloride | 6 g. |

The ingredients were admixed together in a laboratory size ribbon blender for 15 minutes and filled into size 0 gelatin capsules, each capsule containing 620 mg.

FORMULA M

| Ingredient | Amount |
|---|---|
| Aspirin | 325 g. |
| d-Propoxyphene hydrochloride | 65 g. |
| Starch | 218 g. |
| L-Lysine dihydrochloride | 12 g. |

The ingredients were admixed together in a laboratory size ribbon blender for 15 minutes and filled into size 0 gelatin capsules, each capsule containing 620 mg.

TABLE III

FREE SALICYLIC ACID CONTAINED IN PHARMACEUTICAL COMPOSITIONS AFTER FOUR DAYS STORAGE IN FILLED CAPSULES AT 50° C.

| Formula | d-Propoxyphene Hydrochloride mg./Capsule | L-Lysine dihydrochloride mg./Capsule | L-Lysine dihydrochloride as % of d-Propoxyphene Hydrochloride | % Free Salicylic Acid Contained in Pharmaceutical Compositions[1] |
| --- | --- | --- | --- | --- |
| H | 65 | None | — | 1.96 |
| J | 65 | 2 | 3.08 | 1.56 |
| K | 65 | 4 | 6.15 | 1.22 |
| L | 65 | 6 | 9.23 | 1.05 |
| M | 65 | 12 | 18.46 | 0.81 |

[1]Each result is the average of 6 separate assays.

The data indicate that the addition of L-lysine dihydrochloride to a pharmaceutical composition comprising aspirin and d-propoxyphene hydrochloride has a significant effect on the rate of aspirin hydrolysis as measured by the development of free salicylic acid.

EXAMPLE 4

Pharmaceutical compositions comprising 227 mg. aspirin, 162 mg. phenacetin, 32 mg. caffeine, 65 mg. d-propoxyphene hydrochloride, and one of the following stabilizing agents at 3.25 mg., 30 mg. or 84 mg. respectively: glutamic acid, glutamic acid hydrochloride, calcium glutamate tetrahydrate, L-lysine, L-lysine monohydrochloride, calcium L-lysinate, glycine, glycine hydrochloride and calcium lysinate were filled into gelatin capsules. The filled capsules were stored at 50° C. for 4 days and the contents analyzed for free salicylic acid. The free salicylic acid was determined by the following procedure:

A. 1. Empty the contents of one capsule into a screw cap test tube and add the empty capsule to the tube.
2. Add 10.0 ml. of salicylic acid stock solution to the tube, cap tightly and shake vigorously for about 1 minute. Go to next step without delay.
3. Transfer 1.0 ml. of the above sample solution to a second tube.
4. Add 10.0 ml. of ferric nitrate-nitric acid solution to the tube, cap tightly and shake vigorously for about 1 minute.
5. Centrifuge the tube at 2500 r.p.m. for about 2 minutes.
6. Quickly remove a portion of the upper layer and read at 525 nm. versus water. Label this reading "$A_{525}$Sa. + Std."

B. Standard
Repeat steps 3–6 above using the standard stock solution in place of the sample solution in step 3. Label this reading "$A_{525}$Std."

C. Blank
Repeat steps 3–6 above using 1% formic acid in 1,2-dichloroethane in place of the sample solution in step 3. Label this reading "$A_{525}$Blk."

CALCULATIONS $$\frac{(A_{525}sa. + std.) - (A_{525}std.)}{A_{525}std. - A_{525}blk.} \times \frac{mg.std.}{500 \text{ ml.}} \times \frac{1.0 \text{ ml.}}{10.0 \text{ ml.}} \times$$

$$\frac{10.0 \text{ ml.}}{1 \text{ tablet or capsule}} \times \frac{10.0 \text{ ml.}}{1.0 \text{ ml.}} \times$$

$$\frac{100\%}{mg. \text{ A.S.A.®/tablet or capsule}}$$

% non-aspirin salicylates (free salicylic acid, FSA)/dose

REAGENTS NEEDED

1. Formic acid, 98%, A.R.
2. 1,2-dichloroethane
3. 1% Formic acid in dichloroethane. Add 10.0 ml. formic acid to a 1000 ml. volumetric flask, dilute to volume with 1,2-dichloroethane and mix well.
4. Ferric nitrate, [Fe(NO$_3$)$_3$ 9H$_2$O], A.R.
5. Nitric acid, A.R.
6. 0.07 M nitric acid. Transfer 4.3 ml. concentrated nitric acid to a 1 liter volumetric flask containing about 200 ml. deionized water. Dilute to volume with deionized water and mix well.
7. Ferric nitrate solution. Dissolve 1.7 g. ferric nitrate in a 1 liter volumetric flask in 100 ml. of 0.07 M nitric acid and dilute to volume with deionized water.
8. Salicylic acid reference standard
9. Salicylic acid stock solution. Dissolve 68 mg. salicylic acid reference standard in a 500 ml. volumetric flask with 1% formic acid in 1,2-dichloroethane and dilute to volume.

TABLE IV

FREE SALICYLIC ACID CONTAINED IN PHARMACEUTICAL COMPOSITIONS COMPRISED OF ASPIRIN, 227 mg; PHENACETIN, 162 mg; CAFFEINE, 32 mg; d-PROPOXYPHENE HYDROCHLORIDE, 65 mg; AND THE INDICATED STABILIZING AGENT AFTER FOUR DAYS STORAGE IN FILLED CAPSULES AT 50° C.

| Agent | FREE SALICYLIC ACID Mg. STABILIZING AGENT/CAPSULE | | |
| --- | --- | --- | --- |
| | NONE | 3.25 | 30 | 84 |
| CONTROL | 2.55 | | | |
| Glutamic acid | | 2.49 | 3.03 | 4.07 |
| Glutamic acid HCl | | 1.93 | 1.79 | 1.81 |
| Calcium glutamide | | 2.80 | 6.18 | 8.48 |
| L-Lysine | | 4.67 | 10.48 | 10.48 |
| L-Lysine HCl | | 2.38 | 2.57 | 2.57 |
| Calcium L-lysine | | 7.64 | * | * |
| Glycine | | 3.05 | 6.31 | 10.83 |
| Glycine HCl | | 2.24 | 2.34 | 2.54 |
| Calcium glycinate | | 8.73 | * | * |

*Sample deteriorated to the extent no assay was possible

These data clearly show that the addition of the hydrochlorides of glutamic acid, L-lysine and glycine to pharmaceutical compositions comprising aspirin and d-propoxyphene hydrochloride is significantly more effective in reducing the rate of aspirin hydrolysis as measured by the development of free salicylic acid than is achieved when the acids themselves or the calcium salts thereof are added to similar compositions in like amounts.

EXAMPLE 5

Pharmaceutical compositions similar to those described in Example 4 with the exception that calcium aspirin was substituted for aspirin to provide an equivalent amount of the acetylsalicylic acid were prepared and subjected to an identical test. The same procedure as described in Example 4 for the determination of free salicylic acid was followed. TABLE V shows the free salicylic acid determinations.

TABLE V

FREE SALICYLIC ACID CONTAINED IN PHARMACEUTICAL COMPOSITIONS COMPRISED OF CALCIUM ASPIRIN, 251 mg; PHENACETIN, 162 mg; CAFFEINE, 32 mg; d-PROPOXYPHENE HYDROCHLORIDE, 65 mg. AND INDICATED STABILIZING AGENT AFTER FOUR DAYS STORAGE IN FILLED CAPSULES AT 50° C.

| STABILIZING AGENT | FREE SALICYLIC ACID Mg. STABILIZING AGENT/CAPSULE | | | |
|---|---|---|---|---|
| | NONE | 3.25 | 30 | 84 |
| CONTROL | 15.75 | | | |
| Glutamic acid | | 17.33 | 17.16 | 16.57 |
| Glutamic acid HCl | | 17.58 | 17.08 | 17.33 |
| Calcium glutamate | | 17.50 | 17.07 | 15.82 |
| L-lysine | | 17.50 | 16.15 | 17.08 |
| L-lysine HCl | | 17.58 | 17.50 | 18.26 |
| Calcium L-lysine | | 16.25 | 16.17 | 13.21 |
| Glycine | | 17.61 | 17.19 | 15.41 |
| Glycine HCl | | 16.85 | 17.10 | 9.48 |
| Calcium glycinate | | 17.78 | 17.36 | 16.68 |

These data indicate that irrespective of whether the amino acid stabilizing agent is in the acid form, the hydrochloride thereof or the calcium salt, there is no effect in reducing the rate of the formation of salicylic acid from calcium aspirin when the latter is used as the source of the acetylsalicylic acid in the pharmaceutical composition. In fact, calcium aspirin is an unsuitable ingredient in the composition.

Inasmuch as the pharmaceutical composition described in Example 4, absent the stabilizing agent, has been an article of commerce for some 15 years or more, it is abundantly apparent from the data obtained in Example 5 that calcium aspirin would make a pharmaceutically unacceptable composition if it were to be substituted for aspirin as the source of acetylsalicylic acid in the formula.

What is claimed is:

1. The method of inhibiting the hydrolysis of acetylsalicylic acid in a pharmaceutical composition comprising actylsalicylic acid and d-propoxyphene hydrochloride which comprises incorporating glutamic acid hydrochloride into such pharmaceutical composition in an amount of from about 5 to about 130 percent by weight of d-propoxyphene hydrochloride in such pharmaceutical composition.

2. The method of inhibiting the hydrolysis of acetylsalicylic acid in a pharmaceutical composition comprising acetylsalicylic acid and d-propoxyphene hydrochloride which comprises incorporating lysine dihydrochloride into such pharmaceutical composition in an amount of from about 5 to about 130 percent by weight of d-propoxyphene hydrochloride in such pharmaceutical composition.

3. The method of inhibiting the hydrolysis of acetylsalicylic acid in a pharmaceutical composition comprising acetylsalicylic acid and d-propoxyphene hydrochloride which comprises incorporating glycine hydrochloride into such pharmaceutical composition in an amount of from about 5 to about 130 percent by weight of d-propoxyphene hydrochloride in such pharmaceutical composition.

4. The method of inhibiting the hydrolysis of acetylsalicylic acid in a pharmaceutical composition comprising acetylsalicylic acid and d-propoxyphene hydrochloride which comprises incorporating alanine hydrochloride into such pharmaceutical composition in an amount of from about 5 to about 130 percent by weight of d-propoxyphene hydrochloride in such pharmaceutical composition.

5. The method of inhibiting the hydrolysis of acetylsalicylic acid in a pharmaceutical composition comprising acetylsalicylic acid and d-propoxyphene hydrochloride which comprises incorporating aspartic acid hydrochloride into such pharmaceutical composition in an amount of from about 5 to about 130 percent by weight of d-propoxyphene hydrochloride in such pharmaceutical composition.

* * * * *

UNITED STATES PATENT AND TRADEMARK OFFICE
CERTIFICATE OF CORRECTION

PATENT NO. : 4,044,125
DATED : August 23, 1977
INVENTOR(S) : Walter D. Walkling

It is certified that error appears in the above-identified patent and that said Letters Patent are hereby corrected as shown below:

Column 1, line 43, "product" should be --produce--.

Column 2, line 10, "de-propoxyphene" should be --de-propoxyphene--.

Column 3, line 28, "2-2-amino" should be --2-amino--.

Column 5, line 14, "a 50°" should be --at 50°--.

Column 5, line 29, "579 mg." should be --570 mg.--.

Column 10, line 45, the word "stabilizing" should be inserted over the word "agent" in the first column of the table so that it reads --Stabilizing Agent--.

Column 11, line 12, after the word "AND" insert --THE--.

Signed and Sealed this

Sixteenth Day of January 1979

[SEAL]

Attest:

RUTH C. MASON
Attesting Officer

DONALD W. BANNER
Commissioner of Patents and Trademarks